United States Patent [19]
Shapeton

[11] Patent Number: 5,814,043
[45] Date of Patent: Sep. 29, 1998

[54] BIPOLAR ELECTROSURGICAL DEVICE

[75] Inventor: Mark Shapeton, Chestnut Hill, Mass.

[73] Assignee: Mentor Ophthalmics, Inc., Norwell, Mass.

[21] Appl. No.: 709,181

[22] Filed: Sep. 6, 1996

[51] Int. Cl.$^6$ .................................................. A61B 17/36
[52] U.S. Cl. ................................. 606/48; 606/50; 606/41
[58] Field of Search ........................... 606/41, 42, 45–52

[56] References Cited

U.S. PATENT DOCUMENTS

| | | | |
|---|---|---|---|
| 4,548,207 | 10/1985 | Reimels . | |
| 4,732,149 | 3/1988 | Sutter | 606/52 |
| 4,823,791 | 4/1989 | D'Amelio et al. | 606/50 |
| 4,890,610 | 1/1990 | Kirwan, Sr. et al. | 606/51 |
| 5,009,656 | 4/1991 | Reimels . | |
| 5,089,002 | 2/1992 | Kirwan, Jr. | 606/50 |
| 5,267,998 | 12/1993 | Hagen | 606/45 |
| 5,290,285 | 3/1994 | Kirwan, Jr. . | |
| 5,346,491 | 9/1994 | Oertli . | |
| 5,571,100 | 11/1996 | Goble et al. | 606/41 |

OTHER PUBLICATIONS

The Kloti Method, "High Frequency Capsulotomy," Instructions for Use and Operation, Oertli, Switzerland.

Primary Examiner—Michael Peffley
Attorney, Agent, or Firm—Fish & Richardson P.C.

[57] ABSTRACT

A bipolar electrosurgical device includes electrodes that are part of a tip which removable from a handle. The electrodes are configured for connection to electrical contacts when the tip is attached to the handle, and disconnected from the contacts which the tip is detached. The electrodes are mounted on a housing of the tip so that the proximal ends of the electrodes are spaced from each other. The handle has an opening which receives the housing, and a plurality of contacts disposed for connection to the proximal ends of the electrodes when the housing is inserted into the opening. Because the electrodes themselves provide the connection with the electrical components of the handle, there is no need for a separate electrical connector. The tip and the electrodes are economically disposable after, e.g., a single use, while the handle can be reused in multiple surgical procedures with other tips. An inventory of differently-constructed tips (e.g., tips having straight or curved electrodes, or having variously-configured distal ends) may be provided for use with the handle.

25 Claims, 8 Drawing Sheets

BIPOLAR ELECTROSURGICAL DEVICE

BACKGROUND OF THE INVENTION

This invention relates to bipolar electrosurgical devices, and particularly to bipolar electrosurgical devices for eye surgery.

Bipolar electrosurgical devices are typically used for promoting blood coagulation and controlling hemorrhaging during eye surgery. In a typical bipolar electrosurgical device, a pair of electrodes (e.g., an insulated wire disposed within a metal tube) are secured within a plastic handle. The handle is, e.g., an injection molded unit or includes two halves which are glued or ultrasonically welded together. The electrodes extend distally from the handle to a pair of exposed, closely spaced tips. The proximal ends of the electrodes are connected within the handle (such as by wires) to a pair of pins, which protrude from the handle for connection to, e.g., an RF energy source. The RF energy induces current flow through tissue against which the electrode tips are placed, thereby coagulating the tissue.

SUMMARY OF THE INVENTION

This invention features a bipolar electrosurgical device with electrodes which can be easily and conveniently detached from the handle. The electrodes are part of a removable tip of the device and are configured to be connected to electrical contacts when the tip is attached to the handle. That is, the electrodes themselves—rather than a separate electrical connector that must be mounted to the electrodes—provide the connection with the electrical components of the handle. Accordingly, the tip and the electrodes are economically disposable after, e.g., a single use, while the handle can be reused in multiple surgical procedures with other tips.

In one general aspect of the invention, the tip of the device includes a housing, and the electrodes are attached to the housing so that the proximal ends of the electrodes are spaced from each other. The handle has an opening which receives the housing, and a plurality of contacts which are disposed for connection to the proximal ends of the electrodes when the housing is disposed in the opening.

Preferred embodiments may include one or more of the following features.

The housing provides a snap fit with the handle within the opening and is releasably insertable into and removable from the handle in a direction along a longitudinal axis of the housing. The proximal ends of the electrodes frictionally engage the electrical contacts when the housing is disposed in the opening. Thus, inserting a tip into the handle and removing the tip from the handle requires only a simple longitudinal motion on the user's part. And once assembled, the tip and handle are held firmly together by both a friction fit and a snap fit.

The proximal ends of the electrodes are coaxial and axially spaced from one another, as are the electrical contacts in the handle. An insulator is disposed coaxially between the electrodes. The proximal end of the insulator is disposed axially intermediate the axially spaced proximal ends of the electrodes. The electrodes may be substantially straight between their proximal and distal ends, or they may be curved.

The housing includes a protrusion which is received by a corresponding notch on the handle when the housing is inserted into the handle opening. The engagement of the protrusion within the notch provides the snap fit. The protrusion is oriented at a selected radial position with respect to the electrodes. Thus, the engagement of the protrusion in the notch helps ensure that the electrodes are positioned properly with respect to the handle. This feature is particularly useful when the electrodes are curved.

The proximal end of the housing is tapered, and the opening in the handle includes correspondingly tapered sides to receive the proximal end of the housing. The tapered engagement between the housing and the handle helps guide the tip into place during insertion. Grooves on the surface of the handle and housing allow the user to firmly grasp the instrument and avoid losing his or her grip during surgery. The housing is made of plastic, and thus the tip is economically disposable.

The handle includes a plurality of connector pins connected to the electrical contacts. The pins are mounted at the proximal end of the handle, and serve to interconnect the electrosurgical device with a source of, e.g., RF power via a conventional cable.

In another general aspect of the invention, the electrosurgical device is provided with a plurality of the removable tips. Accordingly, the user can choose a tip from an inventory of bipolar tips. This is particularly useful in embodiments in which the tips are configured differently. For example, some tips may be curved in various directions, while other tips are straight. Other tips may have differently-configured electrodes at the distal regions of the tips (e.g., the electrodes may be beveled, or not).

The electrosurgical device is easy to use. The user simply selects a tip and inserts its housing into the handle opening so that the proximal ends of the electrodes become connected to the electrical contacts. The device is then ready for use in surgery. The electrodes are energized by operating power applied to the electrical contacts in the handle via the cable and the connector pins. The resultant current flow between the electrodes at the distal region of the instrument performs the desired tissue treatment (such as coagulation).

After the tissue is treated, the tip may be removed from the handle and discarded. If desired, another tip may be selected, inserted onto the handle, and used to perform a different treatment (e.g., cauterization) during the same surgical procedure. Thereafter, the second tip is removed and discarded. The handle is fully sterilizable (such as by autoclaving) and thus may be reused in subsequent surgical procedures.

Among other advantages, the invention eliminates the need to mount the electrodes on a discrete electrical connector which joins with the handle. As a result, the tips can be economically disposed of after a single procedure, while the handle can be reused for many surgical procedures. Accordingly, the tip housing is conveniently made with a low-cost material designed for a single use (e.g., plastic), while the handle is made from a more rugged material (such as metal or a composite) to withstand repeated use.

The user thus can economically maintain a large inventory of single-use tips and one surgical handle. Moreover, the user may thus choose the most effective tip for a particular surgical treatment from the inventory and employ that tip in the treatment.

Other features and advantages of the invention will become apparent from the following description and from the claims.

BRIEF DESCRIPTION OF THE DRAWINGS

FIG. 6, including

DESCRIPTION OF PREFERRED EMBODIMENTS

Figure 1:
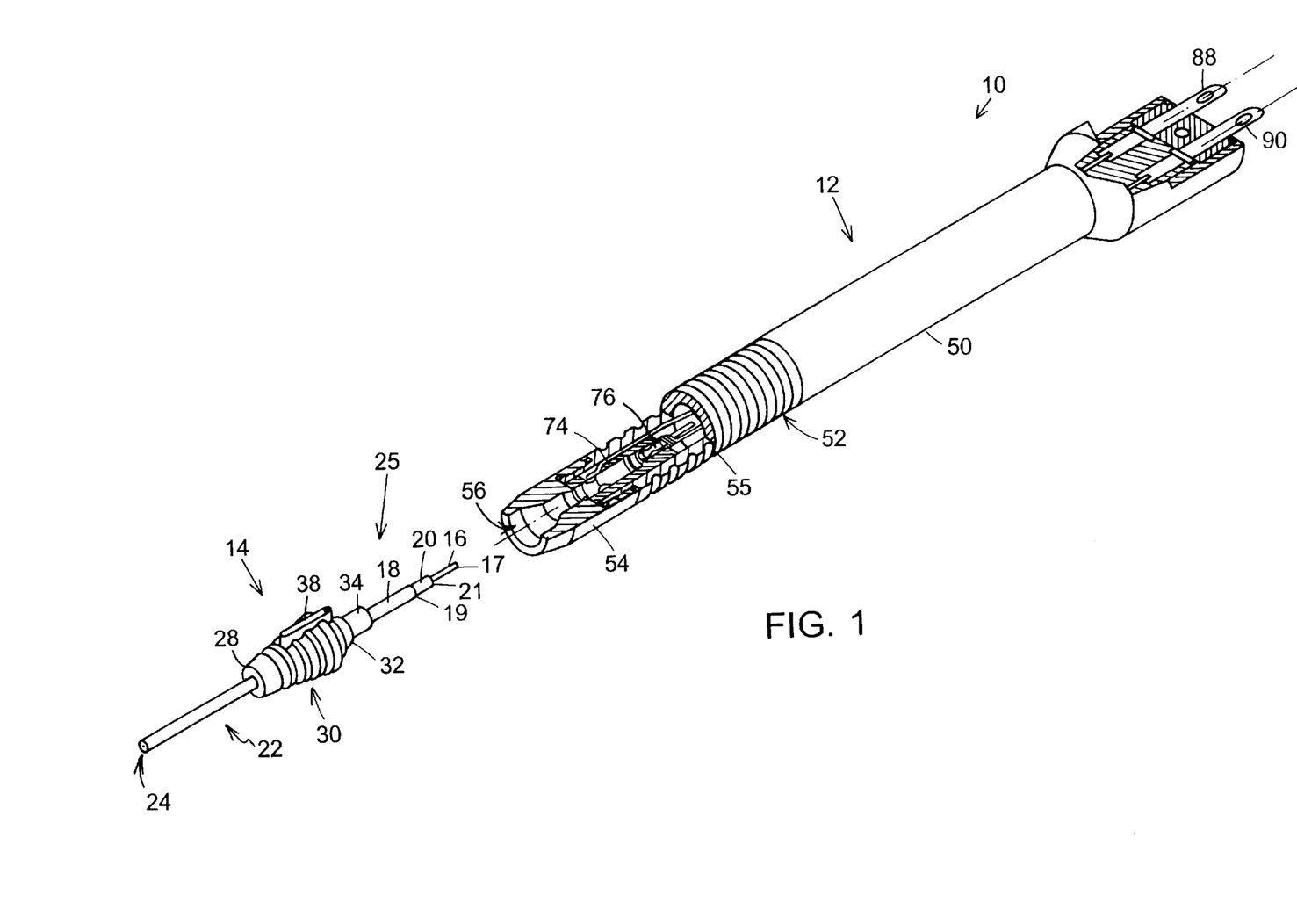
FIG. 1 is a perspective view of a surgical device with a tip of the device separated from a handle, and the handle partially cut away.
Figure 2:
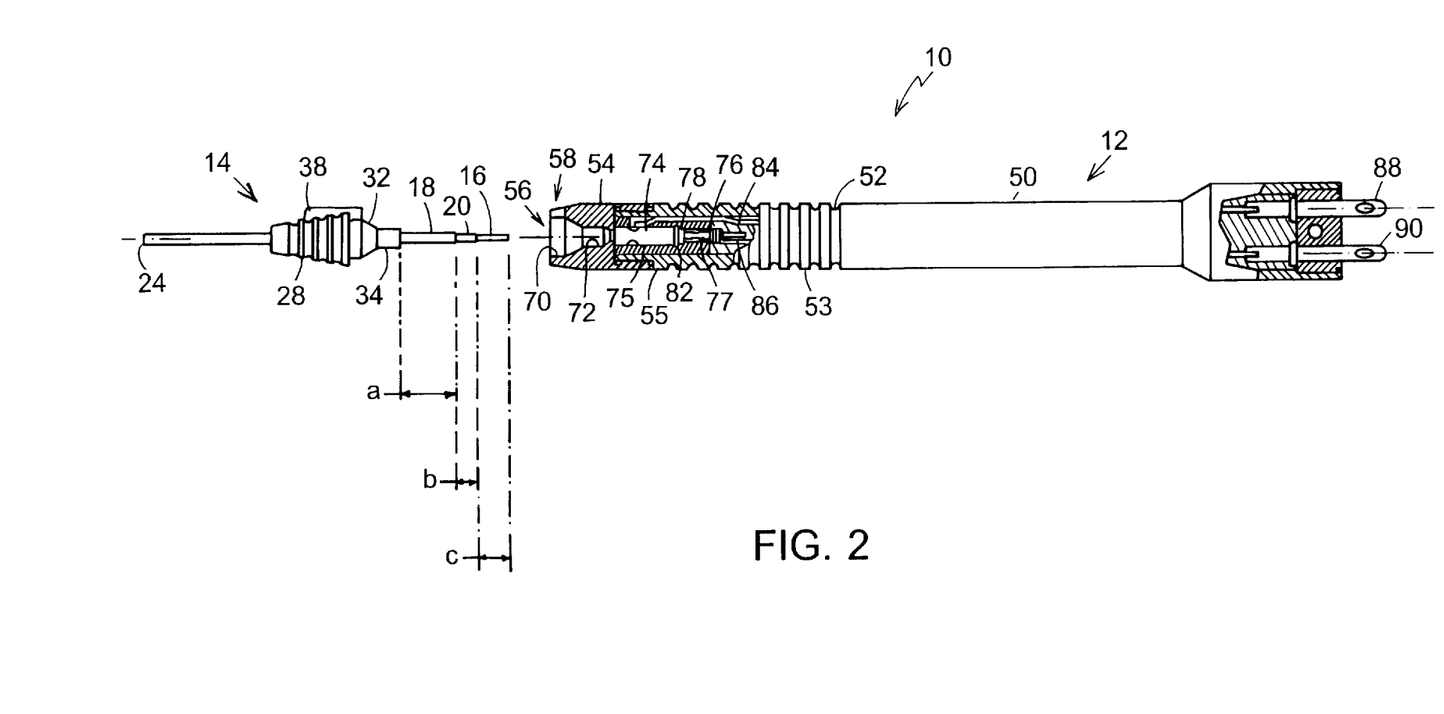
FIG. 2 is a side, partially cross-sectioned view of the tip and handle of FIG. 1.
Figure 3:
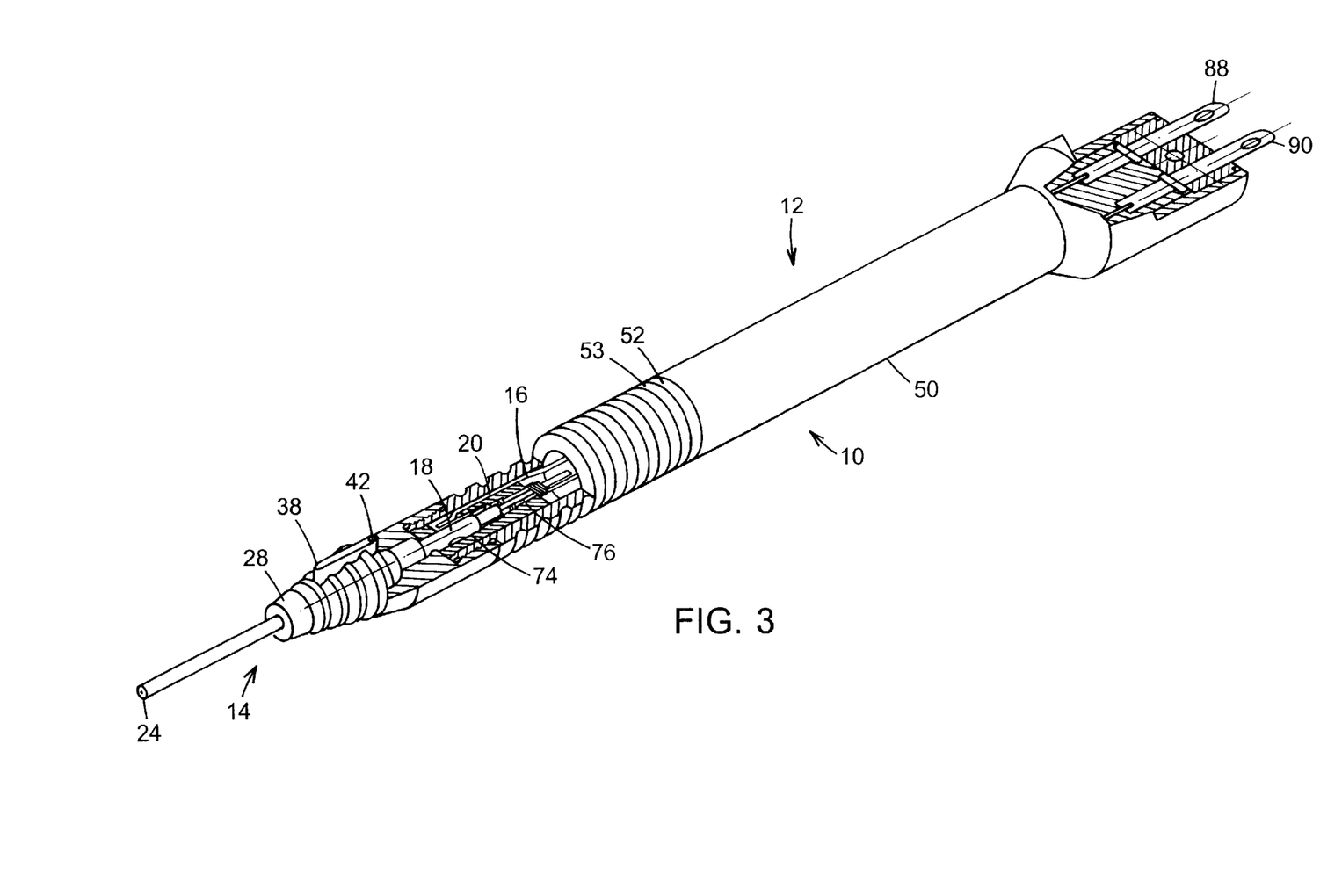
FIG. 3 is a perspective view of the surgical device of FIG. 1 with the tip inserted in the handle.
Figure 4:
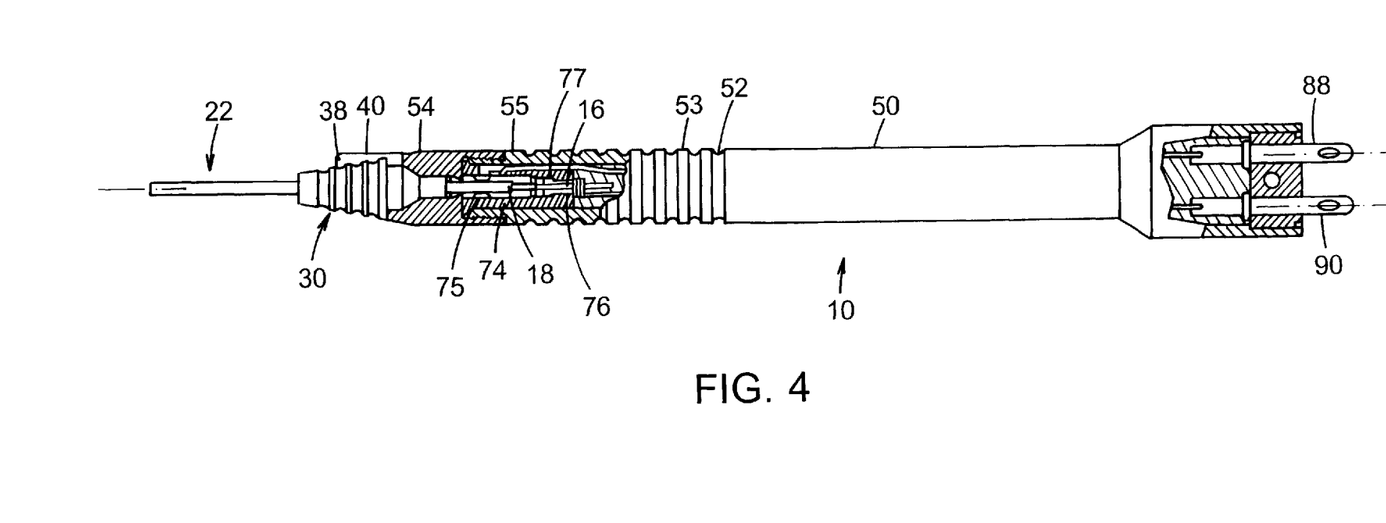
FIG. 4 is a side, partially cross-sectioned view of the device of FIG. 3.

Referring to FIGS. 1 and 2, a surgical device 10 has a reusable handle 12 with a removable tip 14. In use, tip 14 is inserted into handle 12 as shown in FIGS. 3 and 4. After use, tip 14 is removed from handle 12, discarded, and a new tip is inserted into handle 12.

Tip 14 comprises a solid, cylindrical inner electrode 16 disposed coaxially inside a hollow, cylindrical outer electrode 18. Electrodes 16, 18 are closely spaced and separated by a thin coaxial insulator 20. Alternatively, tip 14 may be made by coating outer electrode 18 onto an insulated inner electrode 16, as described in the copending patent application of Harry Reimels et al. entitled "Bipolar Electrosurgical Instrument and Method for Making the Same," filed Jan. 26, 1996 as Ser. No. 08/591,953, assigned to the present assignee and incorporated herein by reference.

A distal treatment end 22 of the electrodes includes a flat surface 24 that is applied to tissue during surgery. A proximal connection end 25 of the electrodes is configured for connection to handle 12. Electrodes 16, 18 form a substantially straight line from connection end 25 to treatment end 22.

At connection end 25, a proximal end 17 of inner electrode 16 is axially displaced from a proximal end 19 of outer electrode 18. A proximal end 21 of insulator 20 is disposed intermediate the proximal ends 17, 19 of electrodes 16, 18. As a result, a length (a) of electrode 18, a length (b) of insulator 20 and a length (c) of electrode 16 are exposed (FIG. 2).

Handle 12 includes an opening 56 at one end. Two cylindrical electrical contacts 74, 76 separated by cylindrical receptacle 78 are arranged coaxially in opening 56. Contact 74 has one end 82 abutting an end of receptacle 78. Another end of receptacle 78 is adjacent to an end of contact 76. Contact 76 has a smaller radius than contact 74, and receptacle 78 has a radius intermediate those of contacts 74, 76.

The length of contact 74 matches the combined lengths of outer electrode 18 and insulator 20 at connection end 25 (i.e. length a+length b in FIG. 2). The length of receptacle 78 and contact 76 together equal the length (c) of electrode 16 exposed at tip end 25.

A ring-like conductor 75, 77 is disposed on the inside surface of each electrical contact 74, 76. The inner diameter of conductors 75, 77 is only slightly larger than the diameter of electrodes 18, 16, respectively. In addition, each contact 74, 76 is connected by a wire 84, 86 to a connector pin 88, 90 at a proximal end of handle 12. Pins 88, 90 are adapted for connection to a high frequency power source.

Tip 14 also includes a plastic housing 28 mounted around the exterior of electrode 18. Treatment end 22 and connection end 25 of electrodes 16, 18 extend distally and proximally, respectively, from housing 28. The distal end of housing 28 is conically shaped and has a sloping, grooved exterior surface 30. A proximal end of housing 14 comprises a conical section 32 that terminates in a cylindrically-shaped nose 34. The shape of handle opening 56 is complementary to that of the proximal end of housing 28 so that housing 28 snugly mates with handle 12. Thus, the distal end of opening 56 includes a conically-shaped inner surface 70 that meets a cylindrically-shaped inner surface 72.

Handle 12 is formed as a cylindrical body 50 (made from, e.g. metal or composite material) with a distal section 54 that is threaded onto a proximal section 55. Opening 56 is disposed in distal section 54, while proximal section 55 includes the electrical contacts 74, 76, receptacle 78, wires 82, 86 and pins 88, 90. A series of grooves 52 is formed in the exterior surface of proximal section 55 to define a set of raised circumferential ribs 53 that assist the user in gripping the device.

Figure 5:
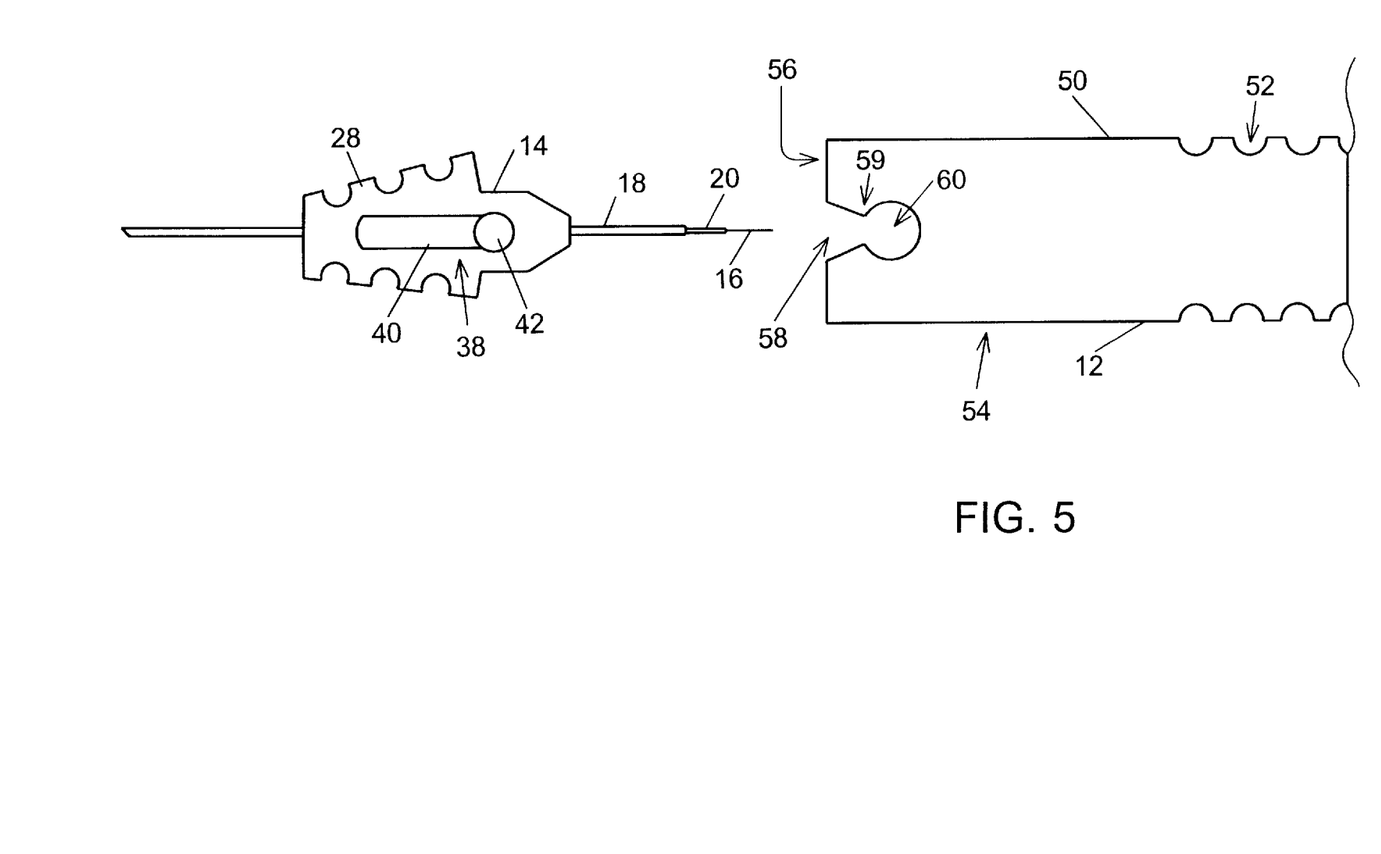
FIG. 5 is an enlarged view of the tip and handle of FIG. 1.
Figure 6A:
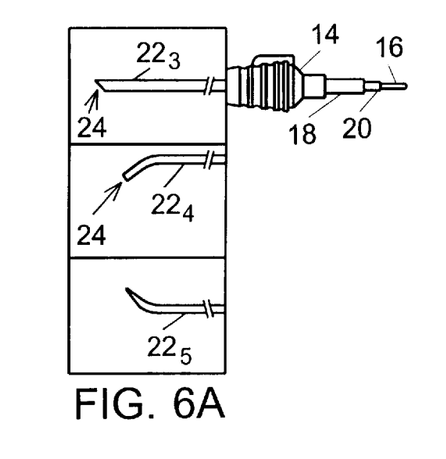
FIGS. 6a, 6b, 6c, 6d and 6e shows a variety of tips for use with the handle of FIG. 1.
Figure 6B:
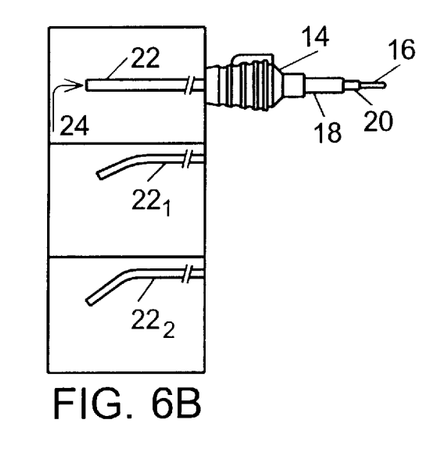
Figure 6C:
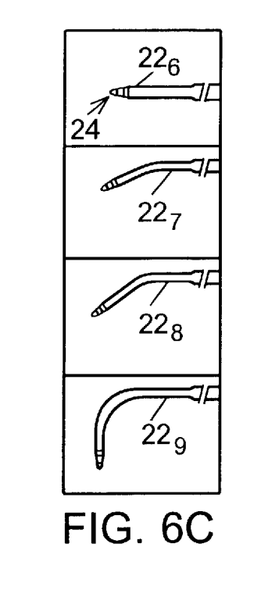
Figure 6D:
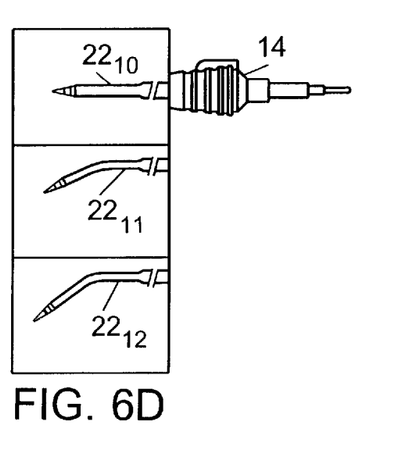
Figure 6E:
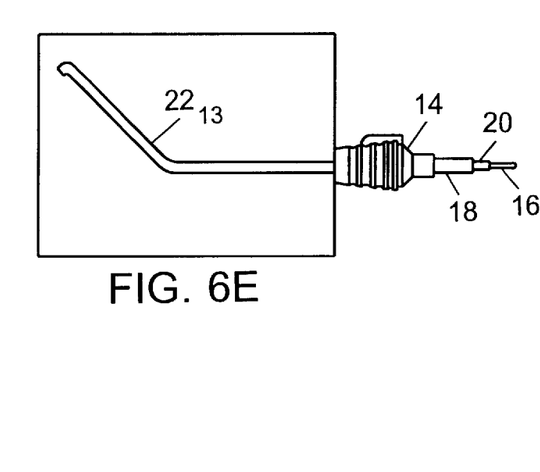

Referring also to FIG. 5, tip 14 includes a protrusion 38 extending from grooved surface 30 to an edge of tapered section 32, at a predetermined radial position with respect to electrodes 16, 18. Protrusion 38 has an axially-extending rectangular tab 40 that terminates proximally in a round button 42. The diameter of button 42 is slightly larger than the width of tab 40.

Distal end 54 of handle 14 includes an axially-extending, tapered slot 58 that communicates with opening 56. The proximal end 59 of slot 58 meets a round opening 60 that is only slightly larger than button 42 on tip 14. The diameter of round opening 60 slightly exceeds the width of slot 58 at end 59.

FIGS. 6a through 6e show an inventory of tips 14 compatible with handle 12. Treatment ends 22 of tips 14 have a variety of configurations. For example, some tips 14 have treatment ends with a flat distal surface 24 (e.g, treatment end 22) which may be beveled (e.g., treatment end $22_3$), while others tips 14 have a concave distal surface 24 (e.g., end $22_4$). Still other tips 14 in the inventory have treatment ends that are tapered to a fine point (e.g., treatment end $22_{10}$), to a round, blunt distal surface 24 (e.g., treatment end $22_6$) or to a flat surface (e.g., end $22_5$). The treatment ends of some tips form a straight line from housing 28 to surface 24 (e.g., end 22), while others include a bend of 30°, 45°, or 90° (e.g., ends $22_7$, $22_6$, $22_9$, respectively). Another type of tip 14 includes a treatment end $22_{13}$ with two bends, appropriate for performing a capsulotomy.

In operation, a user selects a tip 14 from the inventory and inserts the selected tip 14 into handle 12 simply by aligning protrusion 38 on housing 28 with slot 58 in handle 12 and inserting connection end 25 of tip 14 into handle opening 56. The proximal end of housing 12 enters handle opening 56, and protrusion 38 slides into slot 58. As button 42 of protrusion 38 enters round opening 60, end 59 of slot 58 expands. After tip 14 is fully inserted, end 59 of slot 58 snaps back to its original size to hold button 42 firmly in opening 60. The exterior surfaces of housing sections 32, 34 also frictionally engage inner surfaces 70, 72 of opening 56. Tip 14 is thus held in handle 12 by a friction fit as well as by a snap fit.

As tip 14 is being inserted, outer electrode 18 and insulator 20 enter contact 76, and outer electrode 18 firmly contacts conductor 75. Similarly, inner electrode 16 slides into contact 74 and receptacle 78, and proximal end 17 of electrode 16 engages conductor 77. Friction between the adjacent surfaces of electrodes 16, 18 and conductors 77, 75 provides a reliable, secure electrical connection, and also helps avoid tip 14 disengaging from handle 12.

Figure 7:
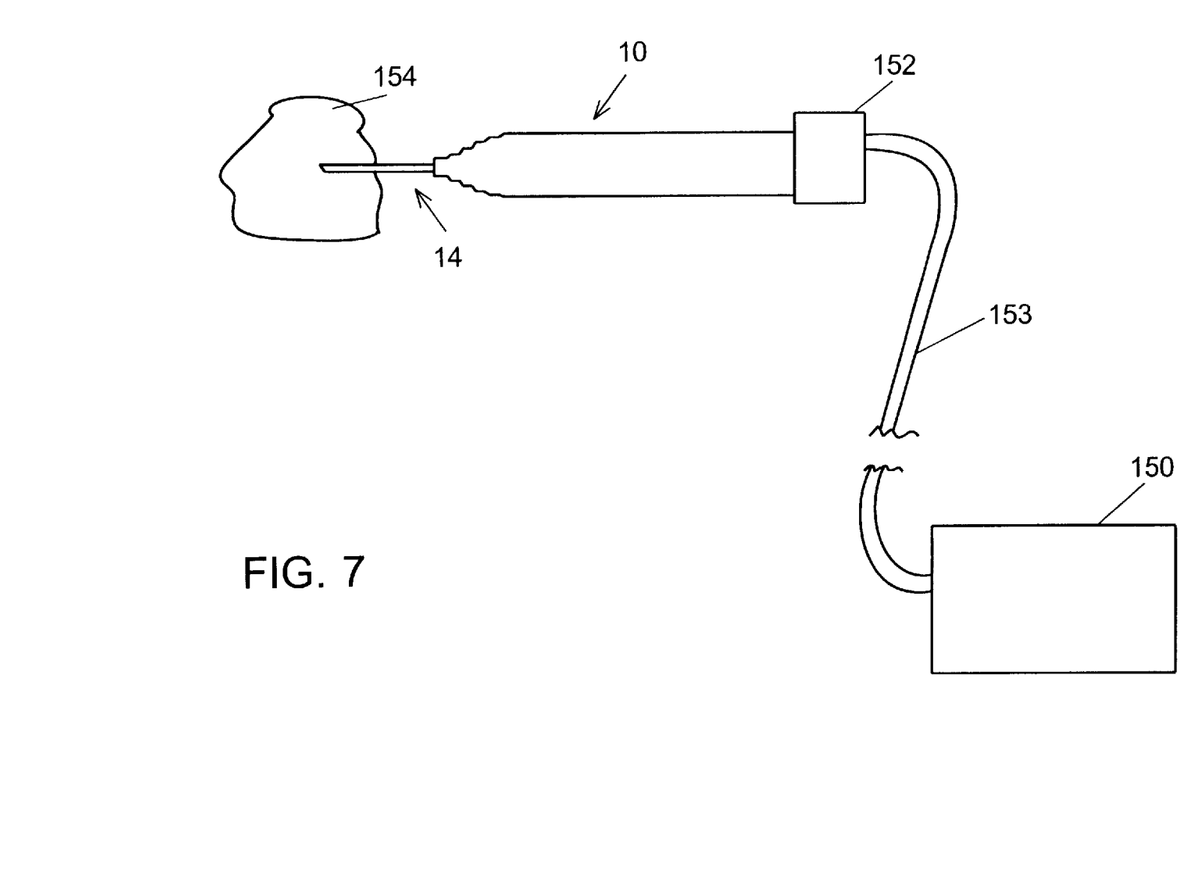
FIG. 7 is a schematic representation of the surgical device of FIG. 1 in use.

Referring to FIG. 7, the user connects device 10 to a high frequency power source 150 by connecting a standard socket 152 on a cable 153 to connector pins 88, 90. Power source 150 provides electrical power to contacts 74, 76 via pins 88, 90, which in turn provide the power to electrodes 16, 18 (FIG. 1). Holding body 50 of handle 12 and housing 28 of tip 14, the user places surface 24 of electrodes 16, 18 on tissue 154 to be treated, e.g., within the eye. The voltage applied by electrodes 16, 18 induces a high frequency current in the tissue, thereby performing cauterization, coagulation, or other surgical operations.

After use, the user detaches tip 14 from handle 12 by pulling tip 14 axially out of opening 56. Protrusion 38 on tip 14 forces edges 59 of slot 58 outward as button 42 is pulled through slot 58. The user discards tip 14, and sterilizes handle 12 (e.g., by autoclaving) for subsequent use.

The user then selects a new tip from the inventory of tips. For example, the user may choose tip 14 with treatment end $22_1$, shown in FIG. 7. The user then inserts the new tip in handle 12, as described above, and performs a new surgical procedure.

Other embodiments are within the following claims. For example, the user may sterilize and reuse tip 14 instead of discarding tip 14 after a single use. In this case, tip 14 would be made from reusable material capable of, e.g., withstanding autoclaving.

Also, proximal section 55 and distal section 54 of handle 12 may be combined into a unitary, molded body.

The handle and tip may have other shapes. For example, referring to FIG. 8, surgical device 100 has a non-cylindrical handle 112 that axially tapers between relatively large diameter regions 112a, 112c and smaller waist regions 112b, 112d. This contoured shape fits comfortably in the user's hand. In particular, narrow waist region 112d can be gripped between the user's fingers to assist in precisely treatment end 122 of tip 114 in the body.

Figure 8:
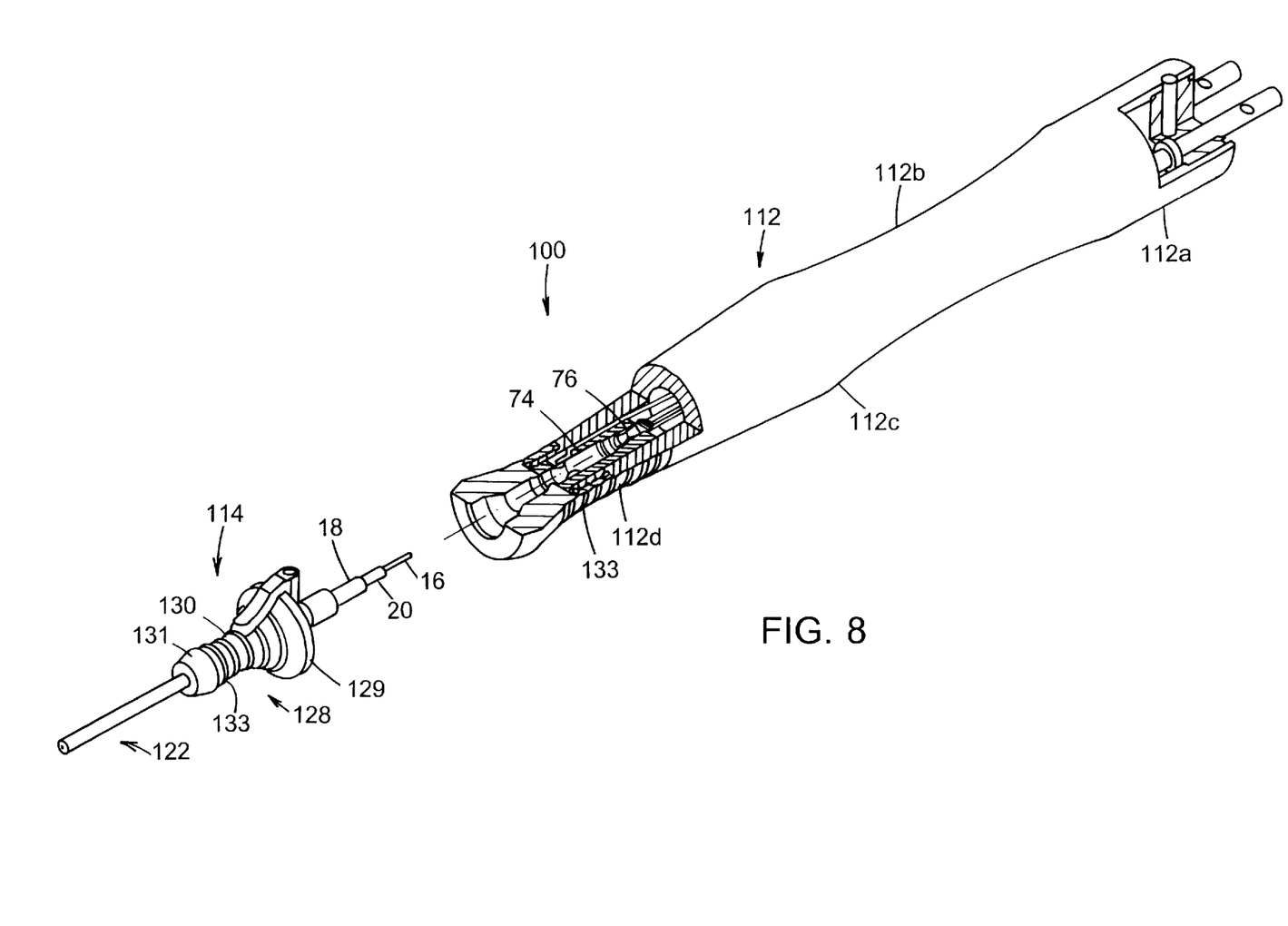
FIG. 8 shows another embodiment of a surgical device and removable tip.

The housing 128 of tip 114 is hourglass-shaped, tapering from a relatively wide proximal region 129 to a narrow intermediate waist 130, and then to a somewhat larger-diameter distal region 131. With this shape, housing 128 fits securely in the user's hand (with waist 130 being gripped between the user's fingers) when inserting tip 114 into and removing tip 114 from handle 112. Both handle 112 and tip housing 128 may be ribbed 133 to further enhance gripping.

What is claimed is:

1. A replaceable tip for a surgical device of the kind that includes a handle having an opening and a plurality of coaxial, axially spaced electrical contacts therein, said tip comprising
    a housing having a proximal end and a distal end, the proximal end of the housing configured to be received within the opening of the handle, and
    a plurality of electrodes disposed through said housing, said electrodes having distal ends that extend distally from the distal end of said housing and proximal ends that are coaxial and axially spaced from each other and that extend proximally from the proximal end of said housing for connection to the coaxial, axially spaced electrical contacts of the handle when the proximal end of said housing is inserted in the opening of the handle, the proximal end of said housing being constructed to be releasably secured to the handle for operation of said surgical device solely by inserting the proximal end of the housing axially into the opening of the handle.

2. The tip of claim 1 wherein said housing is configured to provide a snap fit with the handle.

3. The tip of claim 1 wherein said proximal ends of said electrodes are configured to frictionally engage the electrical contacts when said housing is inserted in the handle opening.

4. The tip of claim 1 further comprising an insulator disposed coaxially between said electrodes, said insulator having a proximal end disposed axially intermediate the axially spaced proximal ends of said electrodes.

5. The tip of claim 1 wherein said housing is plastic.

6. The tip of claim 1 wherein said electrodes are substantially straight between said proximal ends and said distal ends.

7. The tip of claim 1 wherein said electrodes include a bend between said proximal ends and said distal ends.

8. A surgical device comprising
    a tip including a housing having a proximal end and a distal end, and a plurality of electrodes disposed through said housing, said electrodes having proximal ends that are coaxial and axially spaced from each other and that extend proximally from the proximal end of said housing, and distal ends that extend distally from the distal end of said housing, and
    a handle having an opening configured to receive the proximal end of said housing, said handle and the proximal end of said housing being constructed to be releasably secured together for operation of said surgical device solely by inserting the proximal end of said housing axially into said opening, said handle further including a plurality of coaxially and axially spaced electrical contacts disposed for connection to said coaxially and axially spaced proximal ends of said electrodes when the proximal end of said housing is inserted in said opening of said handle.

9. The device of claim 1 wherein said housing is configured to be removable from said opening of said handle solely by withdrawing the proximal end of said housing axially from said opening.

10. The device of claim 9 wherein said housing is configured to provide a snap fit with said handle.

11. The device of claim 1 wherein said proximal ends of said electrodes are configured to frictionally engage said electrical contacts when said housing is disposed in said opening of said handle.

12. The device of claim 1 further comprising an insulator disposed coaxially between said electrodes, said insulator having a proximal end disposed axially intermediate the axially spaced proximal ends of said electrodes.

13. The device of claim 1 wherein said housing comprises a protrusion configured to be received by a corresponding notch on said handle when said housing is inserted in said opening of said handle.

14. The device of claim 13 wherein said protrusion is oriented at a selected radial position with respect to said electrodes, thereby to cause said electrodes to be oriented at said radial position with respect to said handle.

15. The device of claim 1 wherein the proximal end of said housing is tapered, and said opening in said handle includes correspondingly tapered sides to receive said proximal end of said housing.

16. The device of claim 1 wherein said housing comprises plastic.

17. The device of claim 1 wherein said handle further comprises a plurality of connector pins connected to said electrical contacts.

18. The device of claim 17 further comprising a radio frequency power source configured for connection to the connector pins, the connector pins providing power from the power source to the electrical contacts when the pins are coupled to the source.

19. The device of claim 1 wherein said electrodes are substantially straight between said proximal ends and said distal ends.

20. The device of claim 1 said electrodes include a bend between said proximal ends and said distal ends.

21. Apparatus comprising
- a plurality of tips each of which includes a housing having a proximal end and a distal end, and a plurality of electrodes disposed through said housing, said electrodes having proximal ends that are coaxial and axially spaced from each other and that extend proximally from the proximal end of said housing, and distal ends that extend distally from the distal end of said housing, and
- a handle having an opening configured to receive the proximal end of a said housing of a selected one of said tips, said handle and the proximal end of said housing being constructed to be releasably secured together for operation of said surgical device solely by inserting the proximal end of said housing axially into said opening, said handle further including a plurality of coaxially and axially spaced electrical contacts disposed for connection to said coaxially and axially spaced proximal ends of said electrodes when the proximal end of said housing of said selected tip is inserted in said opening of said handle.

22. The apparatus of claim 21 wherein the distal ends of said plurality of tips have different configurations.

23. An electrosurgical method for treating tissue, comprising
- providing a surgical device which includes a handle having an opening and a plurality of coaxial, axially spaced electrical contacts therein,
- providing a plurality of tips for said surgical device, each of said tips including a housing having a proximal end and a distal end, the proximal end of the housing configured for insertion into said opening, and a plurality of electrodes disposed through said housing, said electrodes having distal ends that extend distally from the distal end of said housing and proximal ends that are coaxial and axially spaced from each other and that extend proximally from the proximal end of said housing for connection to said coaxial, axially spaced electrical contacts when the proximal end of said housing is inserted in said opening of said handle,
- selecting one of said tips,
- releasably securing said selected tip to said handle for operation of said surgical device solely by inserting the proximal end of said housing of said selected tip axially into said handle opening so that said proximal ends of said electrodes become connected to said electrical contacts,
- applying power to said electrical contacts to energize said electrodes, and
- treating the tissue with the energized electrodes.

24. The method of claim 23 further comprising
- removing said selected tip from said handle after said treating step,
- selecting a second one of said tips, and
- inserting said housing of said second tip into said handle opening so that said proximal ends of said electrodes become connected to said electrical contacts, and
- repeating said applying and treating steps.

25. The device of claim 23 further comprising removing said selected tip from said opening solely by withdrawing the proximal end of said handle axially from said opening.

* * * * *

UNITED STATES PATENT AND TRADEMARK OFFICE
CERTIFICATE OF CORRECTION

PATENT NO.   : 5,814,043

DATED        : September 29, 1998

INVENTOR(S)  : Mark Shapeton

It is certified that error appears in the above-identified patent and that said Letters Patent is hereby corrected as shown below:

Col. 6, claim 9, line 35, replace "claim 1" with --claim 8--;

Col. 6, claim 11, line 41, replace "claim 1" with --claim 8--;

Col. 6, claim 12, line 45, replace "claim 1" with --claim 8--;

Col. 6, claim 13, line 49, replace "claim 1" with --claim 8--;

Col. 6, claim 15, line 57, replace "claim 1" with --claim 8--;

Col. 6, claim 16, line 61, replace "claim 1" with --claim 8--;

Col. 6, claim 17, line 63, replace "claim 1" with --claim 8--;

Col. 7, claim 19, line 4, replace "claim 1" with --claim 8--;

Col. 7, claim 20, line 7, replace "claim 1" with --claim 8--;

Signed and Sealed this

Second Day of March, 1999

*Attest:*

Q. TODD DICKINSON

*Attesting Officer*      *Acting Commissioner of Patents and Trademarks*